United States Patent [19]

Wisowaty et al.

[11] Patent Number: 4,500,711
[45] Date of Patent: Feb. 19, 1985

[54] SYNTHESIS OF LEUCOVORIN

[75] Inventors: James C. Wisowaty, Chapel Hill; Roy A. Swaringen, Durham; David A. Yeowell, Chapel Hill, all of N.C.

[73] Assignee: Burroughs Wellcome Co., Research Triangle Park, N.C.

[21] Appl. No.: 218,554

[22] Filed: Dec. 22, 1980

Related U.S. Application Data

[63] Continuation of Ser. No. 942,408, Sep. 14, 1978, abandoned, which is a continuation of Ser. No. 779,545, Mar. 21, 1977, abandoned.

[51] Int. Cl.³ ............................................. C07D 475/04
[52] U.S. Cl. .................................................... 544/258
[58] Field of Search .......................................... 544/258

[56] References Cited

U.S. PATENT DOCUMENTS 2,741,608  4/1956  Shive .................................... 544/258

FOREIGN PATENT DOCUMENTS 496012  10/1970  Switzerland .
721742  1/1955  United Kingdom .
733062  7/1955  United Kingdom .

Primary Examiner—Paul M. Coughlan, Jr.
Attorney, Agent, or Firm—Donald Brown

[57] ABSTRACT

In the synthesis of calcium leucovorin (calcium 5-formyl-5,6,7,8-tetrahydrofolate), the use of an amine base in the conversion of anhydroleucovorin (5,10-methenyl-5,6,7,8-tetrahydrofolic acid) to leucovorin unexpectedly results in a pure (USP) product directly from the reaction mixture.

8 Claims, No Drawings

SYNTHESIS OF LEUCOVORIN

This is a continuation of application Ser. No. 942,408, filed Sept. 14, 1978, which is a continuation of application Ser. No. 779,545, filed Mar. 21, 1977, both now abandoned.

SUMMARY OF INVENTION

Calcium leucovorin is useful in diminishing the toxicity and counteracting the effect of inadvertantly administered overdoses of folic acid antagonists and in the treatment of the megaloblastic anemias due to sprue, nutritional deficiency, pregnancy and infancy (Physicians Desk Reference, 31st Edition, 1977, p. 904,905). Calcium leucovorin is a potent agent for neutralizing the immediate toxic effects of Methotrexate and is therefore useful as a "rescue" agent in reversing the peripheral toxic effects of Methotrexate (or other antifols) resulting from its use in anti-neoplastic chemotherapy.

Calcium leucoveoin is an extremely expensive material, mainly because the heretofore available methods of synthesis yielded a final product which required extensive purification in order to pass USP (United States Pharmacopeia) specifications. Almost invariably, the prior art purification has required column chromatography which is a very expensive stage in the preparation of calcium leucovorin for a number of reason. For example, it is time consuming, labor and equipment intensive, and uses exceedingly large volumes of solvent for elution.

It has now been unexpectedly discovered that if an amine base is used to effect ring opening of anhydroleucovorin to give leucovorin, the calcium leucovorin produced therefrom contains substantially lower levels of impurities than if an inorganic base is used. Surprisingly, in most cases calcium leucovorin prepared using an amine base in the ring opening step was sufficiently pure to pass USP specifications after simply filtering, washing, and drying the product, i.e. column chromatgraphy was not required.

An amine base useful in this invention is one which does not give rise to any significant amount of inorganic salts as contaminants of the isolated calcium leucovorin and results in demonstrably less contamination by organic materials as well.

Preferred amine bases include methylamine, triethylamine, morpholine, tetraethylammonium hydroxide, and N,N-diethylethanolamine. Other bases which are suitable but less preferred include ammonia, aniline, p-chloroaniline, n-butylamine, cyclohexylamine, diethanolamine, triethanolamine, diethylamine, dimethylamine, N,N-dimethylaniline, piperidine, piperazine, N-methylpiperazine, N,N'-dimethylpiperazine, pyridine, imidazole, benzylamine, ethylenediamine, o-, m-, and p-toludine, o-, m-, and p-anisidine. In addition it should be understood that those skilled in the art would be able to select other amine bases suitable for use in the process of this invention.

When ammonia is used in the practice of this invention, it may be desirable to operate in pressure equipment to prevent loss of ammonia by evaporation. Indeed, it may be desirable to operate in pressure equipment when using other volatile organic amines as would be well-known to those skilled in the art.

The reaction of this invention comprises mixing 5,10-methenyl-5,6,7,8-tetrahydrofolic acid (anhydroleucovorin), an amine base, and water and heating the mixture at a temperature of from about 50° C. to reflux for a period of time of from about 30 min to about 10 hours, perferably about 4–6 hours, at a pH of from about 5–7 to give leucovorin. The pH of the mixture is adjusted to and maintained at 5 to 7 by the addition or removal, as appropriate, of suitable amounts of the amine bases useful in this invention. The anhydroleucovorin may be used in the form of its internal salt (i.e. zwitterion) or as a salt with a suitable anion, preferably chloride, normally as a hydrate. After the ring opening reaction is complete, the reaction mixture is generally cooled and filtered. Slightly more than an equimolar (to anhydroleucovorin) amount of a water soluble calcium salt, e.g. chloride, bromide, iodide, nitrate, acetate, is then added either as an aqueous solution or as a solid to the filtrate and calcium leucovorin is precipitated by adding a water soluble organic solvent, e.g. a lower alkanol such as methanol, ethanol, isopropanol, or acetone. The calcium leucovorin is than removed by filtration, washed with a suitable solvent such as aqueous ethanol, ethanol, acetone, ether, ethyl acetate or the like and dried. Column chromatography is generally not required since the product so obtained meets or exceeds USP specifications.

EXAMPLE 1

5,10-Methenyl-5,6,7,8-tetrahydrofolic acid, chloride hydrochloride dihydrate (10 g) was added in one portion to a mixture of 40% methylamine (6.5 ml) and water (90 ml) at 60° C. The mixture was heated to reflux and the pH adjusted to 6.0 by distilling out excess base. During the following 4 hour reflux period, the pH was maintained between 5.9 and 6.1 by addition of 40% methylamine. The mixture was cooled to room temperature, slurried with 10 g synthetic magnesium silicate and filtered. The filtrate was stored at −5° C. for 16 hours, brought to room temperature and 2.25 g calcium chloride added. The product was precipitated by addition of 30 ml ethanol and collected by filtration. The cake was washed with 50% aqueous ethanol and with ether and dried under reduced pressure.

Yield: 5.9 g (55%).

hplc analysis-93.1%.

USP (Vol. XIX) Quantitative tlc assay for Calcium leucovorin—96 and 101%.

EXAMPLE 2

5,10-Methenyl-5,6,7,8-tetrahydrofolic acid, chloride hydrochloride dihydrate (20 g) was added in one portion to a stirred mixture of triethylamine (20 ml) and water (100 ml) at 65° C. The mixture was heated to reflux and the pH adjusted to 6.0 by distilling out excess base. The pH was maintained between 5.6 and 6.1 for a 5 hour reflux period by addition of triethylamine. The mixture was stirred at room temperature for 16 hours, slurried for 30 minutes with 15 g synthetic magnesium silicate and filtered. Calcium chloride (4 g) was added to the filtrate. The mixture was cooled in an ice bath and 40 ml ethanol was added. The precipitate was filtered, washed with 40 ml 50% aqueous ethanol, 30 ml ethanol, 30 ml ether and dried under reduced pressure.

Yield: 12.1 g (57%).

hplc analysis—94.5%.

USP (Vol, XIX) Quantitative tlc assay for calcium leucovorin—96.4 and 98.3%.

EXAMPLE 3

5,10-Methenyl-5,6,7,8-tetrahydrofolic acid, chloride hydrochloride hydrate (4 g) was suspended in $H_2O$ (35 ml). The pH of the solution was adjusted to 6.5 by addition of appropriate amounts of morpholine. The mixture was maintained at reflux for 6 hours, cooled, slurried for 20 minutes with synthetic magnesium silicate and filtered. The filtrate was adjusted to pH 8.0 with morpholine and aqueous calcium chloride added (0.9 g in 4 ml). The resultant solution was diluted with ethanol until cloudy and cooled at $-5°$ C. for one hour. The solid was filtered, washed with ethanol (15 ml), ether (20 ml) and dried under reduced pressure.

Yield: 2.43 g (55%).

hplc analysis—83%.

Further dilution of the original mother liquor with ethanol provided a second crop of solid product.

Yield: 0.87 g (20%).

hplc analysis—83%.

EXAMPLE 4

5,10-Methenyl-5,6,7,8-tetrahydrofolic acid, chloride hydrochloride dihydrate (10 g) was added in one portion to a mixture of 20% tetraethylammonium hydroxide (20 ml) and water (100 ml) at 50° C. Additional base (~30 ml) was added to adjust the pH to 6. The mixture was maintained at reflux for 4 hours with the pH kept between 5.5 and 6.0 by addition of tetraethylammonium hydroxide. The pH was adjusted to 6.35 and reflux continued for an additional 16 hours. The mixture was cooled and stirred at room temperature for 24 hours. Synthetic magnesium silicate (15 g) was added, slurried for 30 minutes and filtered off. The solution was diluted to 150 ml with water, pH adjusted to 8.7 with tetraethylammonium hydroxide and SD3A added (50 ml). Calcium chloride (2 g) in a minimum amount of water was dropwise added to the solution. The resultant precipitate was filtered at 5° C., washed with 50% aqueous SD3A (50 ml) and slurried in 200 ml 0.1% tetraethylammonium hydroxide in SD3A for 1 hour. The solid was filtered, washed with acetone and dried under reduced pressure.

Yield: 4 g (38%).

hplc analysis—94.4%.

EXAMPLE 5

5,10-Methenyl-5,6,7,8-tetrahydrofolic acid, chloride hydrochloride dihydrate (20 g) was added in one portion to 100 ml water at 60° C. followed by N,N-diethylethanolamine (14.9 g) which adjusted the pH to 6. The mixture was maintained at reflux for 5 hours and the pH kept between 5.7 and 6.2 by addition of N,N-diethylethanolamine. The mixture was cooled, synthetic magnesium silicate (15 g) added and slurried, and filtered through celite and diluted with 40 ml SD3A. The filtrate was kept at $-5°$ C. for 16 hours, aqueous calcium chloride (4.0 g) was added dropwise to the cold filtrate, and the precipitate filtered, washed with SD3A (100 ml) and with ethyl acetate (100 ml) and dried under reduced pressure.

Yield: 13 g (61%).

USP (Vol. XIX) quantitative tlc assay for Calcium leucovorin 91%.

We claim:

1. The method of preparing calcium leucovorin which comprises the steps of forming a mixture by mixing together anhydroleucovorin, an aqueous solvent, and a sufficient amount of a water soluble organic amine base to bring the pH of the mixture to 5 to 7, heating the mixture at a pH of 5–7 adding to the mixture an amount of a water-soluble calcium salt substantially equimolar to anhydroleucovorin, and isolating calcium leucovorin.

2. The method of claim 1 wherein the amine base is selected from methylamine, dimethylamine, triethylamine, morpholine, trimethylamine, tetraethylammonium hydroxide, N,N-diethylethanolamine, aniline, p-chloroaniline, n-butylamine, cyclohexylamine, diethanolamine, triethanolamine, diethylamine, piperidine, N,N-dimethylaniline, piperazine, N-methylpiperazine, N,N'-dimethylpiperazine, pyridine, imidazole, benzylamine, ethylenediamine, o-toluidine, m-toluidine, p-toluidine, o-anisidine, m-anisidine, and p-anisidine.

3. The method of preparing calcium leucovorin which comprises the steps of forming a mixture by mixing together anhydroleucovorin, an aqueous solvent, and a sufficient amount of a water-soluble organic amine base to bring the pH of the mixture to 5 to 7, heating the mixture at a pH of 5–7, adding to the mixture an amount of a water-soluble calcium salt substantially equimolar to anhydroleucovorin, and isolating calcium leucovorin, wherein the amine base is selected from the group consisting of ethylamine, triethylamine, morpholine, tetraethylammonium hydroxide, and N,N-diethylethanolamine.

4. The method of preparing calcium leucovorin which comprises the steps of forming a mixture by mixing together anhydroleucovorin, an aqueous solvent, and a sufficient amount of a water-soluble organic amine base to bring the pH of the mixture to 5 to 7, heating the mixture at a pH 5–7, adding to the mixture an amount of a water-soluble calcium salt substantially equimolar to anhydroleucovorin, and isolating calcium leucovorin, wherein the amine base is methylamine, triethylamine, or N,N-diethylethanolamine.

5. The method of preparing leucovorin which comprises the steps of forming a mixture by mixing together anhydroleucovorin, an aqueous solvent, and a sufficient amount of a water-soluble organic amine base to bring the pH of the mixture to 5 to 7 and heating the mixture at a pH of 5–7.

6. The method of claim 5 wherein the amine base is methylamine, dimethlamine, triethylamine, morpholine, trimethylamine, tetraethylammonium hydroxide, N,N-diethylethanolamine, aniline, p-chloroaniline, n-butylamine, cyclohexylamine, diethanolamine, triethanolamine, diethylamine, piperidine, N,N-dimethylaniline, piperazine, N-methylpiperazine, N,N'-dimethylpiperazine, pyridine, imidazole, benzylamine, ethylenediamine, o-toluidine, m-toluidine, p-toluidine, o-anisidine, m-anisidine, or p-anisidine.

7. The method of claim 5 wherein the amine base is ethylamine, triethylamine, morpholine, tetraethylammonium hydroxide or N,N-diethylethanolamine.

8. The method of claim 5 wherein the amine base is methylamine, triethylamine, or N,N-diethylethanolamine.

* * * * *